United States Patent [19]

Reinhardt et al.

[11] 4,067,333
[45] Jan. 10, 1978

[54] SYRINGE FOR STORAGE AND APPLICATION OF AT LEAST TWO INJECTION MEDIA

[75] Inventors: Ferdinand Reinhardt; Walter Simonich, both of Vienna, Austria

[73] Assignee: IMMUNO Aktiengesellschaft fur chemisch-medizinische Produkte, Vienna, Austria

[21] Appl. No.: 709,092

[22] Filed: July 27, 1976

[30] Foreign Application Priority Data

Aug. 7, 1975   Austria .................................. 6115/75

[51] Int. Cl.² .............................................. A61M 5/00
[52] U.S. Cl. .............................. 128/218 R; 128/218 P
[58] Field of Search ........... 128/218 R, 218 P, 218 M, 128/218 N, 218 NV, 218 D, 218 DA, 215, 216, 221, 234

[56] References Cited

U.S. PATENT DOCUMENTS

| | | | |
|---|---|---|---|
| 2,305,278 | 12/1942 | Smith | 128/218 M |
| 2,607,344 | 8/1952 | Brown | 128/218 M |
| 3,108,591 | 10/1963 | Kolbas | 128/218 M |
| 3,545,607 | 12/1970 | Keller | 128/218 P X |
| 3,911,916 | 10/1975 | Stevens | 128/218 R |
| 3,916,893 | 11/1975 | DeFelice | 128/218 R |

*Primary Examiner*—John D. Yasko
*Attorney, Agent, or Firm*—Burns, Doane, Swecker & Mathis

[57] ABSTRACT

There is disclosed a syringe for the storage and application of at least two injection media which are to be administered at different parts of a body and at different times. The syringe comprises a cylindrical syringe body and a piston guided slideably therein and being detachably fastened to an actuating rod. At a selectable distance between the piston in its original position and the syringe cone a floating piston is arranged which divides the syringe body into two compartments. For the injection procedure a needle with one pointed end is attached to the syringe cone and after the first compartment has been emptied a double needle is attached to the cone, which double needle pierces the floating piston and thus opens the second compartment.

3 Claims, 4 Drawing Figures

FIG. 2
FIG. 4
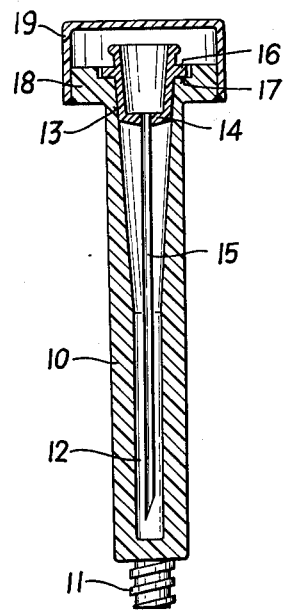
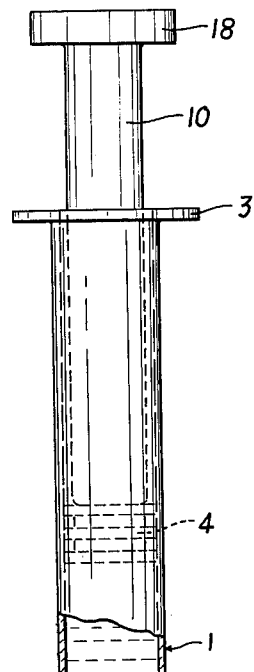
FIG. 1
FIG. 3
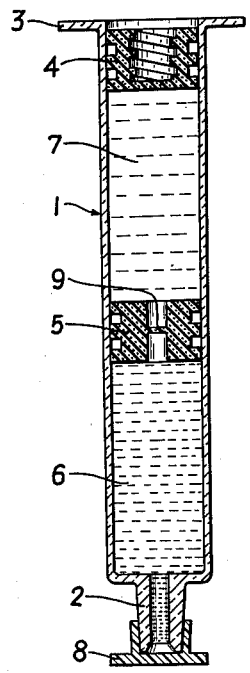
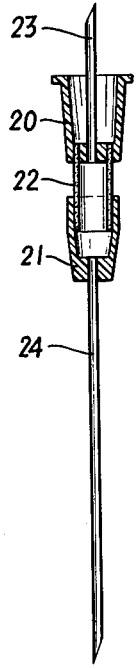

SYRINGE FOR STORAGE AND APPLICATION OF AT LEAST TWO INJECTION MEDIA

This invention relates to a syringe for the storage and application of at least two injection media which are to be administered separate from each other, at different parts of a body and at different times, said syringe comprising a cylindrical syringe body and a piston guided slideably therein and being detachably fastened to an actuating rod.

It has been known to fill media to be injected into a cylindrical syringe body and to store them in said syringe body, wherein the syringe cone is covered or closed, respectively, by a cap and the end of the syringe body lying opposite is covered or closed, respectively, by a rubber plug. The syringe body and the medium to be injected are sterilized in this state and are then stored. When applying the medicament the locking cap is removed, an injection needle is attached to the syringe cone, an actuating rod is connected with the rubber plug then acting as piston and the medicament is applied. Syringes of this type are intended to be used only once. In injection cures they widely diminish the danger of infection caused by mistakes made in the sterilization.

In some cases, e.g. in the simultaneously active and passive immunization, it is necessary to apply different medicaments, such as the antigen and the antibody, which must not be mixed with one another and are not to be injected at the same spot of the body.

Moreover, there are treatments in which the same medicament, as e.g. insuline, is to be administered at different times of the day, e.g. in the morning and in the evening. In said cases it would not be economical to use for each of these injections a syringe of the above-described type, but there is a need to have available with less expenditure the medicaments which are to be administered at different times and at different parts of the body.

It is the object of the invention to create a syringe for the storage of medicaments and for their application at different parts of a body and at different times.

The invention consists in that in a syringe of the above-described type at least one floating piston is arranged within the syringe body at a freely selectable distance between the piston in its original position and the syringe cone, said floating piston separating the syringe body into two syringe-body compartments for taking up the media to be injected, and in that to the syringe cone first an injection needle with one pointed end and then, after the first syringe-body compartment has been emptied, a double needle is attachable, wherein that part of the double needle which reaches into the inner section of the syringe body pierces the floating piston and thus opens the second syringe-body compartment.

It has already been known to arrange in a syringe body apart from the piston having the form of a rubber stopper and being connected with the actuating rod a second, floating piston in front of a by-pass, which forms a groove-shaped recess in the wall of the syringe cylinder, whereby the syringe body is divided into two compartments which are connectable by means of the by-pass. This type of syringe serves the purpose of taking up two media that are incompatible while being stored but are to be mixed prior to injection. In the injection procedure the floating piston is pushed into the range of the by-pass by means of the hydraulic pressure of the first piston, whereupon on further actuating the first piston the two media contained in the syringe-body compartments are mixed with one another. Since the injection is effected at the same spot of the body and at the same time, respectively, this type of syringe is not suited for the object of the invention.

According to an advantageous embodiment of the invention the floating piston consists of a rubber stopper having an inner bore, said inner bore being closed by a thin membrane. Suitably the membrane consists of the same material as the stopper and forms a unity with it. The membrane is advantageously situated in the center, i.e. in the center of gravity of the stopper, whereby the filling of syringes by machines is made easier.

All components of the syringe are made of materials which are capable of being sterilized and are pyrogen-free, in particular the syringe body is made of glass and the piston of rubber.

According to a preferred embodiment the inner bore of the floating piston has a diameter which is slightly bigger than the perforation part of the double needle. The advantage thereof consists in that a clearance space, in which a major quantity of injection liquid remains, is eliminated.

Further advantageous features of the syringe of the invention consist in that the actuating rod is provided with a closable inner space for accommodating one of the injection needles, in that the actuating rod is connected by means of a screw connection with the piston closing the second syringe-body compartment, and in that the mouth of the cone bore facing the syringe is widened in the form of a funnel.

For carrying out the invention, i.e. for applying medicaments at different parts of a body and at different times one needs, as has already been mentioned, at least one double needle having a continuous hollow space, which double needle is after having emptied the first syringe-body compartment attached to the cone of the syringe body and after piercing the floating piston opens a second, respectively a further syringe-body compartment. Such double needles are known per se. They may consist of a thin tube having a continuous hollow space and pointed ends lying opposite each other, wherein between the pointed ends a connection piece being either cone-shaped or having a threaded part is provided for fastening the double needle to the syringe cone. Such double needles have been used e.g. for blood-letting into evacuated containers.

According to a preferred embodiment of the invention the double needle is constructed in such a way that between the injection- or punctuation part, respectively, and the perforation part of the double needle a tube-shaped transparent intermediate part is provided, said intermediate part having a connection piece capable of being attached to the syringe cone. This transparent intermediate part of the double needle has the advantage that it makes it possible to check the position of the punctuating point of the neddle. After piercing the floating piston in the opening of the second syringe-body compartment it is easy to ascertain by aspiration of a small volume, whether the needle point of the punctuating part lies within a vessel or not.

These and other features of the invention will now be described in greater detail with reference to the accompanying drawings in which FIG. 1 shows the syringe body prepared for storing two injection media, FIG. 2 illustrates the actuating rod together with an injection needle and a locking cap, and FIG. 3 shows a double needle necessary for actuating the syringe.

FIG. 4 illustrates the injection procedure.

All illustrations are longitudinal sections.

In FIG. 1 a cylindrical syringe body is denoted with 1, which syringe body terminates at one end in a cone 2 and is at its other end provided with a flange 3. The syringe body is closed by a rubber stopper 4 and another rubber stopper 5 which may be arranged at any spot to be selected between the stopper 4 and the syringe cone 2 divides the syringe body into a first syringe-body compartment 6 and a second syringe-body compartment 7. The cone 2 is covered by a locking cap 8. In the compartments 6 and 7 there are two injection media which are not to be injected at the same part of the body nor at the same time. The rubber stopper 4 closing the syringe body is provided with an inner thread and the rubber stopper 5 separating the two compartments from one another possesses an inner bore which is closed by a thin membrane 9. After the two compartments of the syringe body have been filled with the two injection media the syringe body is sterilized in the state as illustrated in FIG. 1. In the consumption package there is enclosed in addition to the syringe body an acutating rod with a needle as is shown in FIG. 2. The actuating rod 10 is provided at its lower end with a screw thread 11 capable of being screwed into the inner thread of the rubber stopper 4. Moreover, in the actuating rod there is a hollow space 12 which widens conically at its upper end. Into this conically widening part 13 the connection piece 14 of an injection needle 15 can be inserted. The connection piece 14 is provided with a flange 16, which rests on a step-like onset 17 of the pressure- respectively punching plate 18. The pressure respectively punching plate and the connection piece of the injection needle are covered by a cap 19 being connected with the pressure- respectively punching plate in such a way, e.g. welded, that it can be removed only once. Thus the sterile state of the needle is guaranteed.

The consumption package further contains an antiseptically packed double needle. Between the connection piece 20 of the perforation part 23 and the holder 21 of the injection- respectively punctuating part 24 of such a needle a transparent tube 22 is inserted.

The method of using the syringe of the invention is illustrated in FIG. 4. After removing the locking cap 8 from the syringe body and after screwing the actuating rod 10 into the rubber stopper 4 by means of the thread 11, the first needle 15, which has been taken from the interior of the actuating rod, is attached to the syringe cone 2 and the medium contained in the syringe-body compartment 6 is injected to the patient. Thereafter the needle is removed, the double needle according to FIG. 3 is taken out of its package and is attached to the syringe cone 2. In order to make it easier to insert the perforation part 23 of the double needle into the syringe cone the mouth of the cone bore facing the syringe widens in form of a funnel. This phase is shown in FIG. 4, and it can be observed that the perforation part 23 of the double needle pierces the membrane 9 of the second rubber stopper 5, which acts as floating piston, and has thus opened the second syringe-body compartment 7. After aspiration of a small volume and after checking the injection needle the second medium can be administered to the patient.

What we claim is:

1. A syringe set for storing at least two injection media and for separately administering said at least two injection media at different locations or at different times, which comprises:

a cylindrical syringe body terminating in a syringe cone at a forward end thereof;

a first piston slidably disposed within said cylindrical syringe body;

at least one second piston floatingly arranged within said cylindrical syringe body between said first piston and said syringe cone, said at least one second piston dividing the cylindrical syringe body into at least first and second compartments, each to accommodate one injection medium, said first compartment located ahead of said second piston and said second compartment located behind said second piston;

a single pointed needle means detachably securable to said syringe cone for administration of the injection medium of said first compartment;

an actuating rod securable to said first piston for advancing said first and second pistons to eject the injection medium of said first compartment through said single pointed needle means;

a double pointed needle means securable to said syringe cone following removal of said single pointed needle means, said double pointed needle means comprising a puncture portion and a perforation portion, the perforation portion being of a length to extend into said cylindrical syringe body and pierce said advanced second piston, for communicating the injection medium behind said second piston with said puncture portion and enable the administration of the last-named injection medium through said puncture portion in response to further advancement of said first piston.

2. A syringe set as set forth in claim 1, wherein said at least one second piston has an inner bore closed by a thin membrane to be pierced by the perforation portion of said double pointed needle means, said inner bore having a diameter that is only slightly bigger than the cross section of the perforation portion of said double pointed needle means.

3. A syringe set as set forth in claim 1, wherein said double pointed needle means comprises a transparent, tube-shaped part arranged between said puncture portion and said perforation portion.

* * * * *